US00PP27416P2

(12) United States Plant Patent
Delabroye

(10) Patent No.: US PP27,416 P2
(45) Date of Patent: Nov. 22, 2016

(54) ***HEUCHERA* PLANT NAMED 'DELA 051'**

(50) Latin Name: ***Heuchera* hybrid**
Varietal Denomination: Dela 051

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 92 days.

(21) Appl. No.: 14/544,005

(22) Filed: Nov. 13, 2014

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

Upov Pluto Plant Variety Database Apr. 6, 2016, retrieved on Apr. 12, 2016, retrieved from the Internet at <www3.wipo.int/pluto/user/en/index.jsp> 1 page.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Dela 051', that is characterized by its vigorous growth habit, its leaves that are a mix of caramel and light orange-brown in color, its very large leaves, and its white flowers on dark-red flowering stems.

2 Drawing Sheets

Botanical classification: *Heuchera* hybrid.
Cultivar designation: 'Dela 051'.

BACKGROUND OF THE INVENTION

The present invention relates to a new and distinct cultivar of *Heuchera* of hybrid origin, botanically known as a *Heuchera* and is hereinafter referred to by its cultivar name 'Dela 051'.

The new cultivar arose from a cross made by the Inventor in Hantay, France in June of 2010 between 'Caramel' (U.S. Plant Pat. No. 16,560) as the female parent and 'Bronze Beauty' (not patented) as the male parent. The Inventor selected 'Dela 051' as a single unique plant amongst the seedlings that resulted from the above cross in summer of 2011.

Asexual propagation of the new cultivar was first accomplished under the direction of the Inventor by in vitro propagation initiated from meristem tissue in Rijswijk, The Netherlands in November of 2013. Asexual propagation of the new cultivar by in vitro propagation has shown that the unique features are stable and reproduced true to type in successive generations.

SUMMARY OF THE INVENTION

The following traits have been repeatedly observed and represent the characteristics of the new cultivar. These attributes in combination distinguish 'Dela 051' as a new and unique cultivar of *Heuchera*.

1. 'Dela 051' exhibits a vigorous growth habit.
2. 'Dela 051' exhibits leaves that are a mix of caramel and light orange-brown in color.
3. 'Dela 051' exhibits very large leaves.

4. 'Dela 051' exhibits white flowers on dark-red flowering stems.

The female parent of 'Dela 051', 'Caramel' differs from 'Dela 051' in having leaves that are smaller in size, in having a shorter plant habit, and in having leaves that are lighter in color. The male parent of 'Dela 051', 'Bronze Beauty' differs from 'Dela 051' in having leaves that are bronze-brown in color. 'Dela 051' can be most closely compared to the *Heuchera* cultivars 'Pinot Gris' (U.S. Plant Pat. No. 19,592) and 'Orange Blush' (not patented). Both are similar to 'Dela 051' in foliage coloration. 'Pinot Gris' differs from 'Dela 051' in having a much shorter plant habit, in having a less vigorous growth habit, and in having leaves that are greyed-yellow in color with yellow-green veins. 'Orange Blush' differs from 'Dela 051' in having a much shorter plant habit, a less vigorous growth habit, and leaves that are greyed-orange in color.

BRIEF DESCRIPTION OF THE DRAWINGS

The accompanying colored photographs illustrate the overall appearance and distinct characteristics of the new *Heuchera*. The photographs were taken of a plant three years in age as grown outdoors in a 40-cm container in Hantay, France.

The photograph in FIG. 1 provides a side view of the plant habit of 'Dela 051'.

Figure 1:
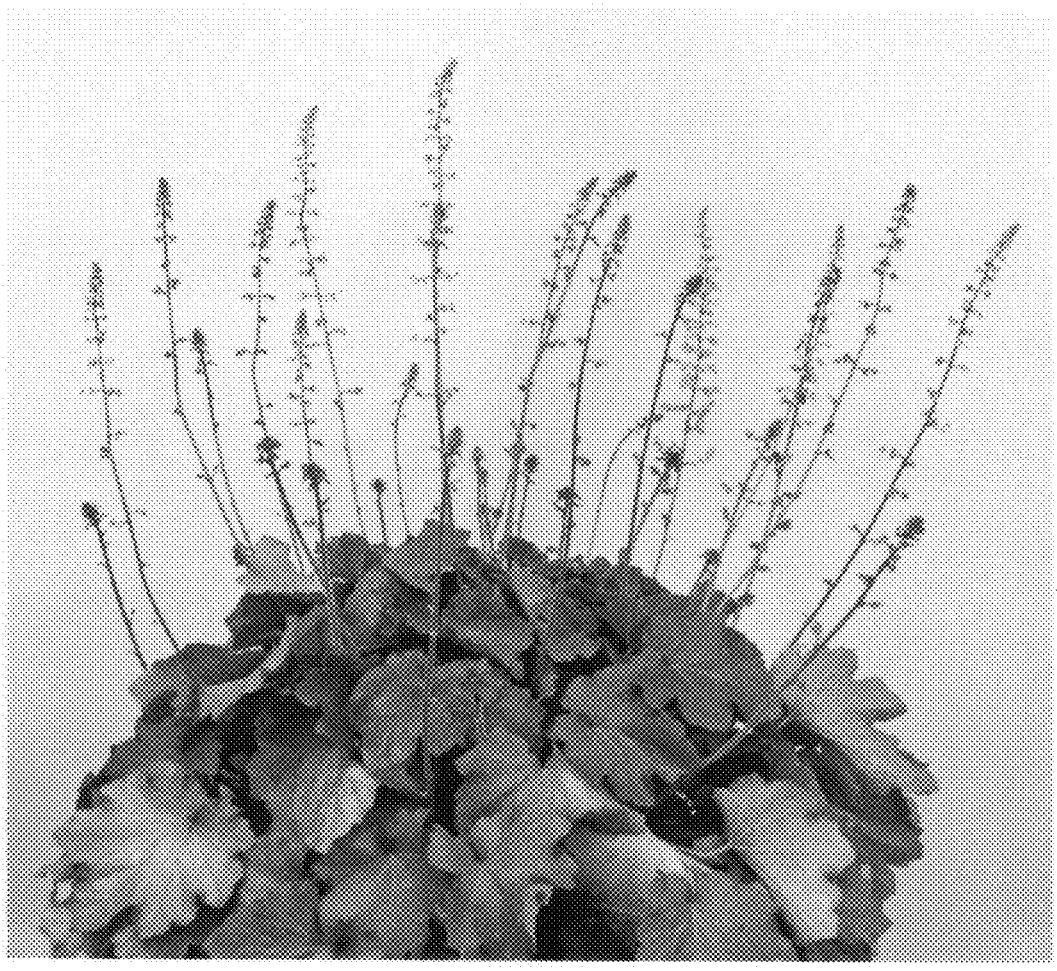
Figure 2:
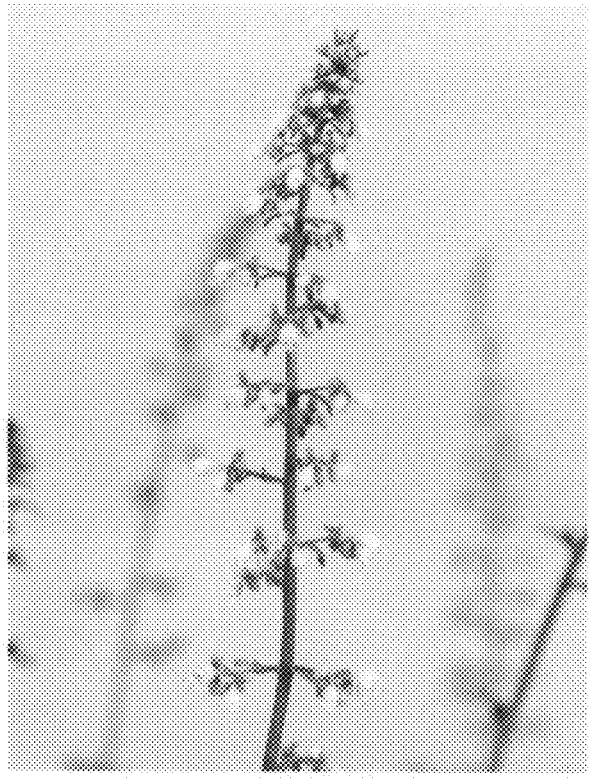

The photograph in FIG. 2 provides a close-up view of an inflorescence of 'Dela 051'.

Figure 3:
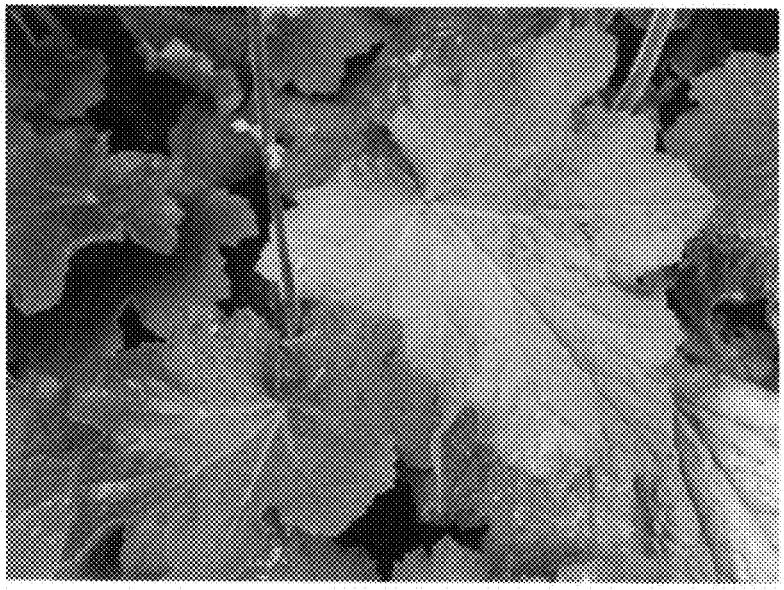

The photograph in FIG. 3 provides a close-up view of the foliage of 'Dela 051'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of three-year old plants of the new cultivar as grown outdoors in a 40-cm container in Hantay, France. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Approximately four weeks in late spring to early summer in The Netherlands.

*Plant type.*—Herbaceous perennial.

*Plant habit.*—Clump-forming, mounded foliage.

*Height and spread.*—An average of 90 cm in height and 100 cm in width.

*Hardiness.*—U.S.D.A. Zones 3 to 9.

*Diseases and pests.*—Similar susceptibility and resistance to pests and diseases as other *Heuchera* varieties.

*Root description.*—Fine and fibrous.

*Propagation.*—In vitro propagation.

*Growth rate.*—Vigorous; flowering stem grow an average of 20 cm per month in spring.

*Root development.*—A plant will fully develop from a rooted tissue culture plantlet in a 7-cm container in 6 to 8 weeks (depending on time of year).

Stem description (peduncle, flowering stem):

*Shape.*—Round.

*Stem color.*—A blend between 182B and 199C.

*Stem size.*—An average of 3.5 mm in diameter and 76.2 cm in length.

*Stem strength.*—Moderately strong.

*Stem aspect.*—Flowering stems grow at an average angle of 75° to soil level (=0°), secondary peduncles grow in an average angle of 85° to main peduncle.

*Stem surface.*—Moderately glossy, densely covered with soft hairs; an average of 0.5 mm in length and 156D in color.

*Stem number.*—Average of 35 main stems per 40-cm container.

*Branching habit.*—Flowering stem emerge from basal rosettes, no lateral branches.

Foliage description:

*Leaf shape.*—Orbicular.

*Leaf division.*—Simple.

*Leaf base.*—Hastate, touching to slightly overlapping.

*Leaf apex.*—Broad acute.

*Leaf venation.*—Laciniate, color upper surface; 161A and lower surface; 195A.

*Leaf margins.*—Shallowly lobed, average of 7 lobes per leaf, lobe margins bi-crenate.

*Leaf attachment.*—Petiolate.

*Leaf arrangement.*—Alternate in basal rosettes.

*Leaf orientation.*—Horizontal to slightly downward to the petiole.

*Leaf surface.*—Both surfaces dull, upper surface moderately covered with soft hairs, 1.5 mm in length and 156D in color, lower surface densely covered with soft hairs especially on main veins and secondary veins, 2 mm in length and 156D in color.

*Leaf color.*—In the spring, young leaf upper surface; ranging between 173A, 174A and 175A, young leaf lower surface; between 184C and 185C, in the summer and fall mature leaf upper surface; ranging between 153A and 199A, mature leaf lower surface; 182B, in the winter upper surface color fades to a blend between 162A and 152D and 152A on the lower surface.

*Leaf size.*—An average of 17.7 cm in length and 18.9 cm in width.

*Leaf quantity.*—An average of 34 per basal rosette.

*Petioles.*—An average of 33.2 cm in length and 4 mm in width, color 178A, older petioles 177B, surface covered with dense soft pubescence, average of 4 mm in length and 156D in color.

*Stipules.*—Small leafy stipules at the base of each leaf, broadly acute apex, with an average of 2.1 cm in length, 4 mm in width and 183D in color.

Flower description:

*Inflorescence type.*—Numerous small bell-shaped flowers arranged on pyramidal panicles on flower scapes emerging from the base of the rosette.

*Inflorescence size.*—An average of 33.9 cm in height (excluding peduncle, measured from lowest flower to the top), average length from base of peduncle to the top is 77.1 cm and 6.8 cm in width.

*Inflorescence number.*—An average of 20 per 40-cm container.

*Flower fragrance.*—None.

*Flower quantity.*—Average of 480 flowers per inflorescence.

*Flower lastingness.*—Average of one week.

*Flower buds.*—Broadly elliptic in shape, an average of 3 mm in length and 2 mm in diameter, color ranging between 155A and 158D, lower half (immature calyx) 164D.

*Flower aspect.*—Outward to slightly nodding.

*Flower type.*—Campanulate.

*Flower size.*—About 6 mm in depth and 5 mm in diameter.

*Petals.*—An average of 5, rotate arrangement and implanted in the hypanthium at base, oblanceolate, recurved and slightly twisted in shape, margin is entire, apex is acute, 3 mm in length and 1 mm in width, upper and lower surface is matte and glabrous, color of upper and lower surface when opening and fully open; NN155D.

*Calyx.*—Campanulate, 4 mm in length and 3 mm in diameter.

*Sepals.*—5, fused into hypanthium, oblong in shape, entire margin, apex is obtuse, base is fused, average of 4 mm in length and 1.5 mm in width, color; immature upper surface N155B, base 75D, immature lower surface NN155A, base in between 155A and N155B, mature upper surface N155B, base 75D, mature lower surface NN155A, base a color in between 155A and N155B, hypanthium has matte surfaces, outside surface densely covered with short hairs; average of 0.5 mm in length and 155A in color.

*Pedicels.*—Average of 2 mm in length and 0.5 mm in width, a blend between 182A to 182C and 199D in color, moderate strength, average angle of 35° (0°=straight on top of secondary peduncle), glabrous surface.

Reproductive organs:

*Gynoecium.*—2 pistils, an average of 3.5 mm in length, stigma is pointed in shape, 164D in color, styles, and average of 3 mm in length and 157D in color, ovaries are 146D in color.

*Androcoecium.*—About 5 stamens, anthers are ovate in shape, 0.3 mm in length and 26B in color, filament an average of 4 mm in length and NN155D in color, pollen is low in quantity and 22A in color.

*Seed and fruit.*—None observed to date.

It is claimed:

1. A new and distinct cultivar of hybrid *Heuchera* plant named 'Dela 051' as herein illustrated and described.

* * * * *